(12) United States Patent
Stone et al.

(10) Patent No.: US 6,387,130 B1
(45) Date of Patent: May 14, 2002

(54) SEGMENTED LINKED INTERVERTEBRAL IMPLANT SYSTEMS

(75) Inventors: Corbett W. Stone, San Diego; James F. Marino, La Jolla, both of CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/549,779

(22) Filed: Apr. 14, 2000

Related U.S. Application Data (60) Provisional application No. 60/129,703, filed on Apr. 16, 1999.

(51) Int. Cl.$^7$ .................................................. A61F 2/44
(52) U.S. Cl. ................................................. 623/17.16
(58) Field of Search ........................... 623/17.11, 17.16, 623/16.11

(56) References Cited

U.S. PATENT DOCUMENTS

| | | |
|---|---|---|
| 5,192,327 A | 3/1993 | Brantigan |
| 5,217,497 A | 6/1993 | Mehdian |
| 5,571,190 A * | 11/1996 | Ulrich ..................... 623/16.11 |
| 5,702,454 A | 12/1997 | Baumgartner |
| 5,755,797 A | 5/1998 | Baumgartner |
| 5,954,769 A * | 9/1999 | Rosenlicht ............... 623/16.11 |
| 6,159,211 A * | 12/2000 | Boriani .................... 623/16.11 |
| 6,200,347 B1 * | 3/2001 | Anderson ................ 623/16.11 |

* cited by examiner

*Primary Examiner*—Michael J. Milano
(74) *Attorney, Agent, or Firm*—Jonathan Spangler (57) ABSTRACT

A method of positioning a plurality of intervertebral implants in a patient's intervertebral space, comprising: introducing an elongated member into the patient's intervertebral space; and sequentially advancing a plurality of intervertebral implants over the elongated member and into the patient's intervertebral space, the plurality of intervertebral implants each having at least one hole passing therethrough, with the elongated member received through the holes passing through each of the plurality of implants.

34 Claims, 10 Drawing Sheets

SEGMENTED LINKED INTERVERTEBRAL IMPLANT SYSTEMS

CROSS-REFERENCES TO RELATED APPLICATIONS

The present application is a regular patent application of and claims the benefit of priority from U.S. Provisional patent application Ser. No. 60/129,703 filed Apr. 16, 1999, the full disclosure of which is incorporated herein by reference.

TECHNICAL FIELD

The present invention is related to spinal fixation and stabilization systems in general and to intervertebral implant systems for promoting arthrodesis in particular.

BACKGROUND OF THE INVENTION

Stabilization of vertebrae relative to each other, primarily for the purposes of indirect nerve decompression and fusion (arthrodesis), is an well-accepted surgical objective. To date, most methods entail a two staged process of intervertebral distraction and then subsequent interposition of either a cortical bone graft or an inorganic implant to maintain the relative position of the vertebrae during the healing phase of arthrodesis.

Many variations of this basic surgical technique exist. Unfortunately, these systems often require considerable time and effort for successful implant placement. This is frequently due to the fact that such systems typically require both excessive surgical tissue dissection and mechanical vertebral distraction such that the various stabilization component(s) of the system can be successfully positioned in a patient's intervertebral space.

In addition, the dimensional constraints typically imposed by access considerations are often in conflict with the desire to place the largest implant possible to support the loads transmitted across the vertebral endplates. Specifically, the larger the implant inserted, the greater the amount of resulting tissue damage both in the intervertebral space, and in the surrounding tissues.

An additional problem with many intervertebral implant devices is that they do not confer a proper lordotic relationship between the vertebrae, either as a consequence of their geometry or their insertion method.

SUMMARY OF THE INVENTION

The present invention provides an intervertebral implant system, comprising; a plurality of implants, each implant having at least one hole passing therethrough; and an elongated member dimensioned to pass through the holes in each of the plurality of implants. In a preferred method, the plurality of intervertebral implants are positioned in a patient's intervertebral space by; introducing the elongated member into the patient's intervertebral space; and sequentially advancing a plurality of intervertebral implants over the elongated member and into the patient's intervertebral space.

In preferred aspects of the invention, the elongated member comprises a cord, string, tether or suture which is used to hold together the plurality of intervertebral implants such that together they form an implant assembly which is positioned between two adjacent vertebrae.

In preferred aspects, each of the intervertebral implants have ends which are angled such that when the implants are pulled or pushed together, they will tend to form a generally C-shaped assembly, which may easily be positioned between two vertebral endplates around the curved perimeter of the patient's intervertebral space.

As will be explained, another advantage of the present system is that the degree of curvature exhibited by the C-shaped implant assembly can itself be selected by selecting implants which are dimensioned with their ends being disposed at preferred angles.

Another important advantage of the present system is that it can be deployed through a narrow operating cannula. As such, the present system advantageously permits the placement of a load supporting implant assembly over a large area between two of the patient's vertebrae, but without requiring that a large diameter access portal pass through the patient and into the patient's intervertebral space.

Therefore, the present system is ideally suited to be introduced into a patient in a minimally invasive surgical procedure, with minimal disturbance to the soft musculature and ligament tissue structures in the spinal region. In contrast, the placement of existing intervertebral implant systems typically compromises such tissues.

Another important advantage of the present system is that it provides an assembly (comprising a plurality of intervertebral implants) which can easily be positioned around the curved perimeter of the patient's intervertebral surface, such that the assembly is positioned on the denser portion of the vertebral endplates (i.e.: the perimeter) to provide enhanced support between the two adjacent vertebrae.

In an optional preferred aspect, at least some of the plurality of individual intervertebral implants have top and bottom surfaces which are angled to one another such that the plurality of intervertebral implants form an assembly which tapers in a lordotic angle when the implants are abutted together end-to-end. Therefore, another advantage of the present system is that the overall implant assembly can preferably be shaped to provide a proper lordotic angle between the adjacent vertebrae when positioned therebetween.

In various optional aspects of the invention, a positioning rod can be used to position each of the separate implants. In one aspect, the separate implants are pushed tightly together, such that they form a C-shaped assembly.

In additional aspects, the elongated member passing through each of the implants can be withdrawn or tightened such that the individual implants are tightened together to abut tightly against one another end-to-end.

As will be explained, an operating cannula(e) and a surgical guideframe for positioning the operating cannula(e) may also preferably by used.

Other advantages of the present system include reduction both in the amount of vertebral distraction and tissue dissection required, thereby decreasing surgical time, complexity and trauma to the patient.

DESCRIPTION OF THE SPECIFIC EMBODIMENTS

The present invention provides systems, devices and methods for placing a plurality of intervertebral implants within a patient's intervertebral space, such that the individual implants form an implant assembly which is ideally suited to promote spinal fusion (arthrodesis) and to provide load bearing stabilization between adjacent vertebrae.

Figure 1:
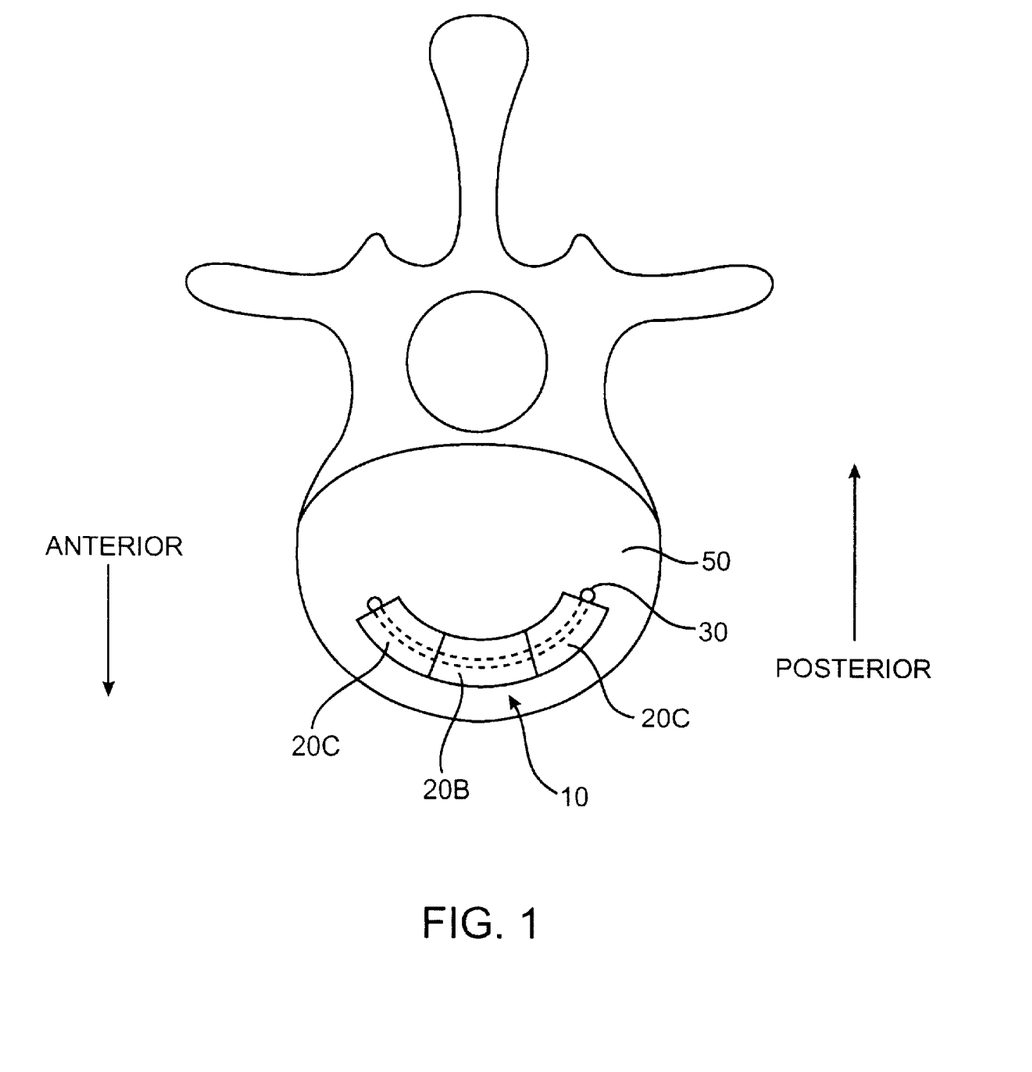
FIG. 1 is a top (sagittal) plan view of a support assembly comprising a plurality of intervertebral implants positioned together around the anterior perimeter of a patient's vertebral endplate in accordance with the present invention.
Figure 2:
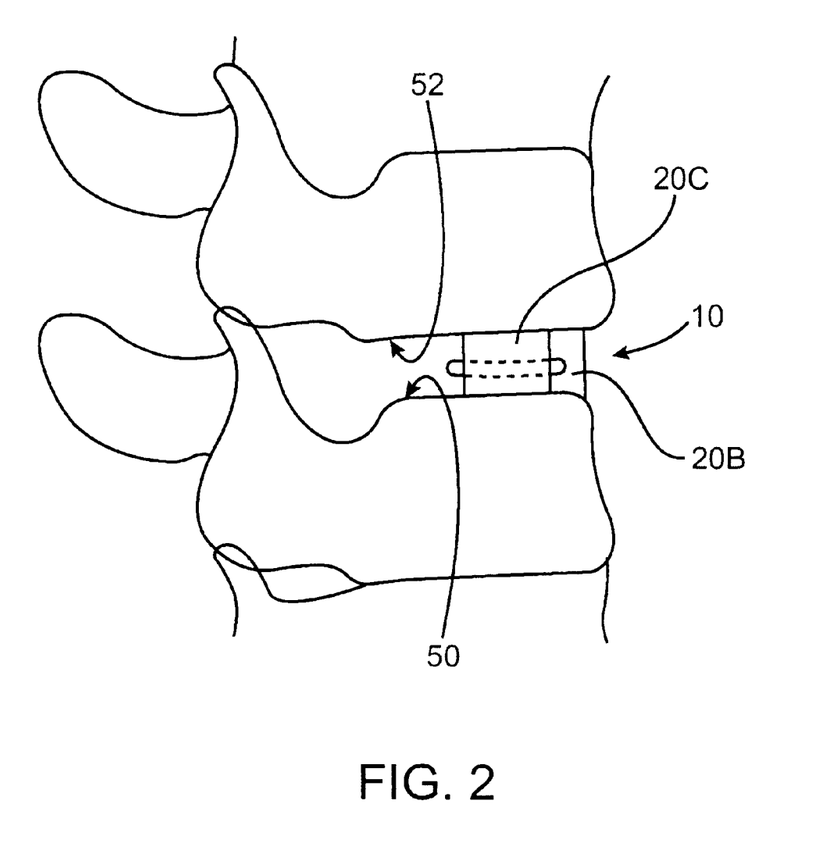
FIG. 2 is a side (lateral) view corresponding to FIG. 1.

Referring to FIG. 1, the present invention provides a generally C-shaped assembly 10 which is preferably positioned to provide support between adjacent vertebral endplates 50 and 52 (FIG. 2). Implant assembly 10 is formed from a plurality of separate individual intervertebral inserts 20A, 20B, and 20C which have been pushed together end-to-end, abutting one another as shown.

It is to be understood that different number of individual implants can be assembled to form implant assembly 10, depending upon the particular dimensions both of the individual implants and the patient's intervertebral space. Accordingly various implant assemblies having 3 (FIG. 1), 5 (FIG. 4A) and 6 (FIG. 6) are shown, and the present invention is not limited to any particular number of individual implants.

Returning to FIG. 1, each of individual intervertebral implants 20A, 20B, and 20C are preferably formed with at least one hole (21 in FIG. 7) running therethrough. An elongated member 30 is threaded through holes 21 on each of intervertebral implants 20A, 20B, and 20C such that implants 20A, 20B, and 20C can be sequentially advanced thereover, as will be explained.

Figure 3:
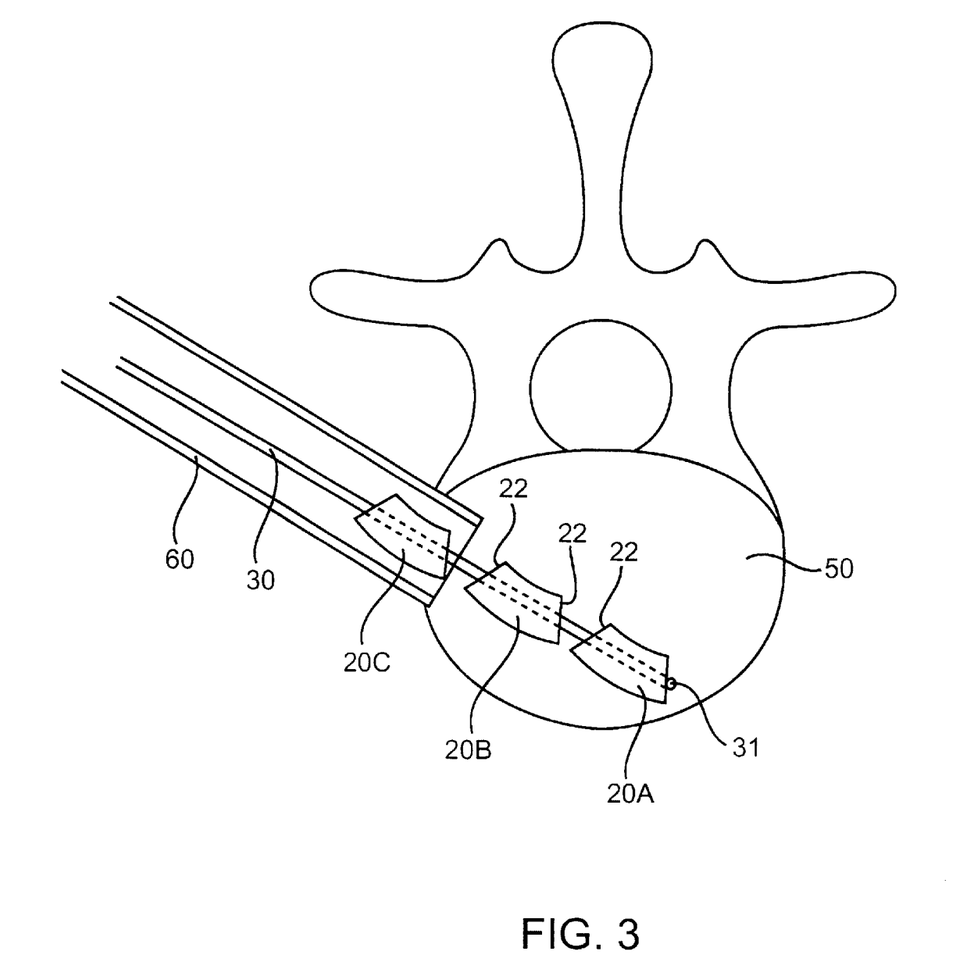
FIG. 3 is a top (sagittal) plan view of the intervertebral implants of FIG. 1 being sequentially advanced over an elongated member.

Referring to FIG. 3, elongated member 30, (which may preferably comprise a wire, string, cord, tether or suture), is first advanced (for example, through cannula 60) into a patient's intervertebral space. Thereafter, implants 20A, 20B, and 20C are then sequentially introduced thereover. Elongated member 30 preferably has an enlarged end (in the case of the member being a wire) or a knot 31 (in the case of the elongated member being a suture) at its distal end. Therefore, implant 20A will come to rest at the distal end of member 30 when advanced thereover, as shown.

Figure 4A:
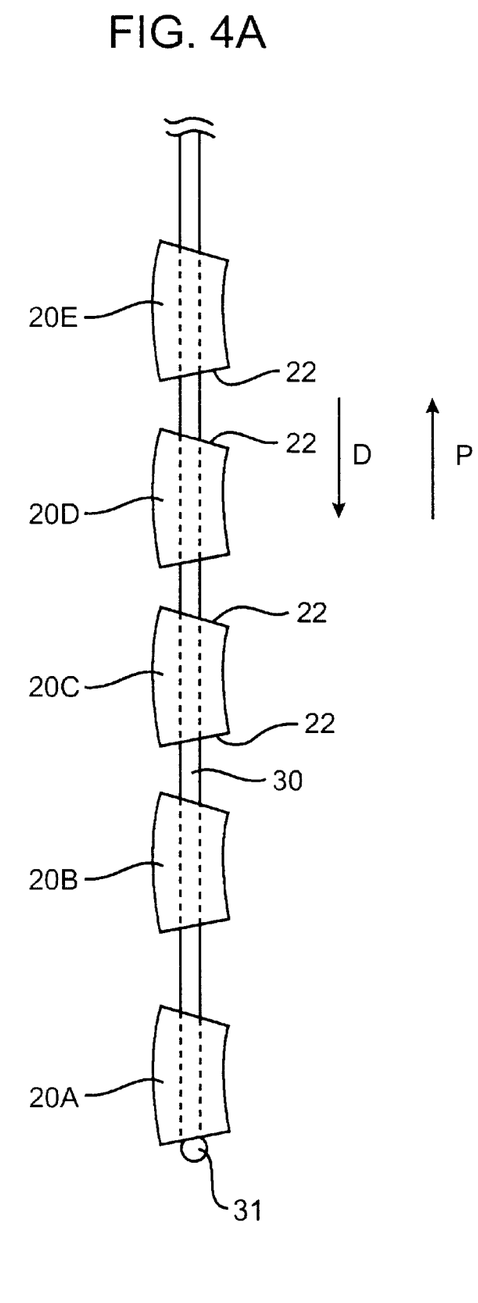
FIG. 4A shows a plurality of intervertebral implants spaced apart on an elongated member.
Figure 4B:
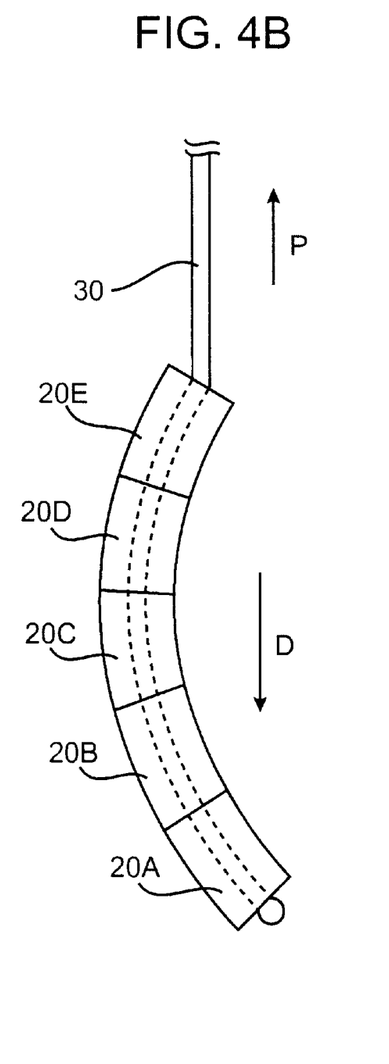
FIG. 4B shows a plurality of intervertebral implants pushed together on an elongated member.

Thereafter, the plurality of intervertebral inserts will be pushed tightly together such that their angled ends 22 will abut against one another, causing assembly 10 to assume a curved C-shape as seen in FIG. 1. FIG. 4A shows the formation of a curved implant assembly 10 in more detail. Specifically, as shown in FIG. 4A, a plurality of intervertebral implants 20A, 20B, 20C, 20D and 20E are advanced distally in direction D over elongated member 30 until implant 20A abuts against knot 31. Thereafter, as shown in FIG. 4B, by either or both of :(1) pushing implant 20E in distal direction D, or (2) pulling elongated member 30 in proximal direction P, angled ends 22 of each of implants 20 will abut together causing assembly 10 to assume a curved C-shape.

Figure 5:
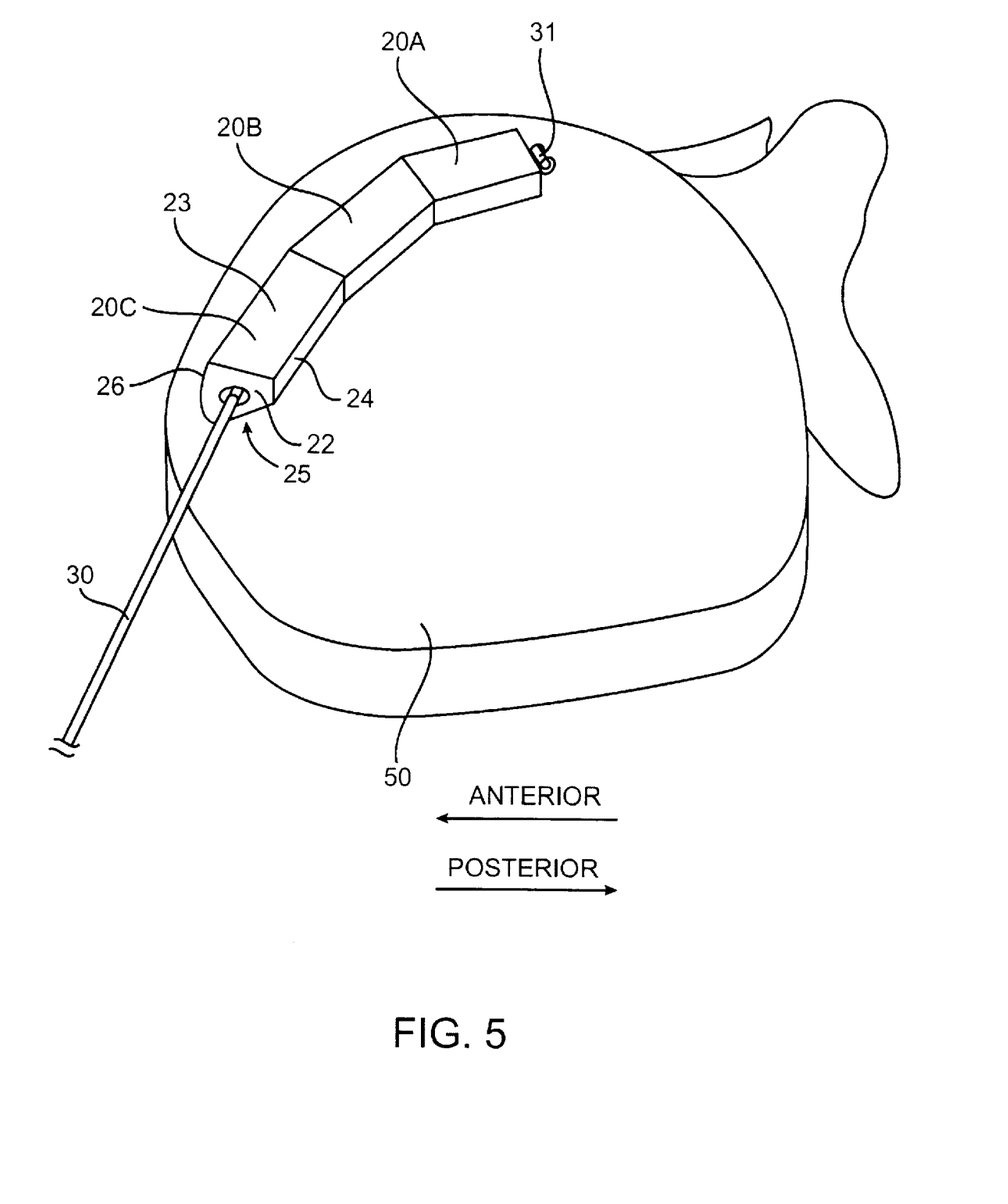
FIG. 5 is a perspective view showing 3 implants positioned on top of a vertebral endplate.

An advantage of assembly 10 assuming a curved C-shape is that it can easily be positioned at a location around the anterior perimeter of vertebral endplate 50, as shown in FIGS. 1 and 5. Moreover, the present invention can be assembled within the patient's intervertebral space to provide support to a large area between vertebral endplates 50 and 52, without the diameter of cannula 60 limiting the size of the assembly.

In various aspects of the invention, elongated member 30 comprises a monofilament or braided suture. Alternatively, elongated member 30 may comprise a flexible wire, which may optionally be made of a shape memory metal such as Nitinol™ As such, wire 30 may be pre-formed to assume a desired curved shape when introduced into the patient's intervertebral space such that the plurality of implants can easily be sequentially introduced thereover.

Referring to FIG. 5, each of the plurality of intervertebral implants can be dimensioned such that when pulled or pushed together to form an implant assembly, the implant assembly will maintain a proper lordotic angle between the adjacent vertebrae, as follows. Implant 20C (which is adapted to be positioned approximately at the lateral mid line through the vertebral endplates) may have a short or narrow first (interior) side 24, and a tall or wide (exterior) side 26, such that top 23 and bottom 25 are angled such that implant 20C assumes a tapered shape to maintain a proper lordotic angle between vertebral endplates 50 and 52 (not shown).

Figure 6:
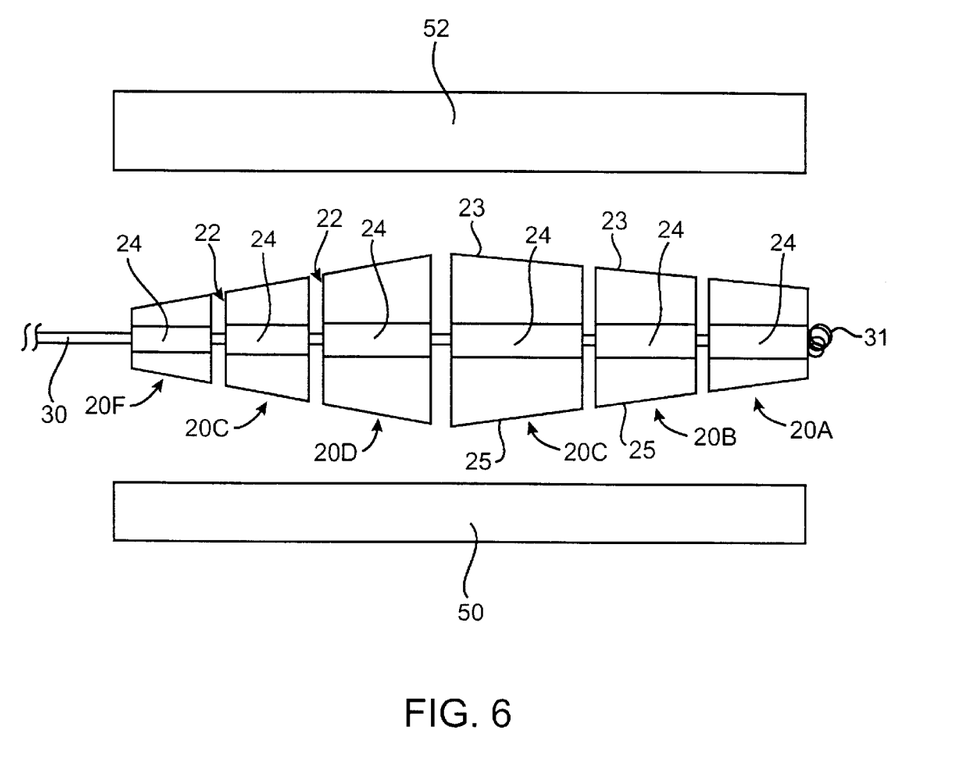
FIG. 6 is a schematic illustration of a plurality of intervertebral implants positioned between two vertebral endplates in an anterior-posterior view.

Referring to FIG. 6, each of the plurality of intervertebral implants can be dimensioned such that when pulled or pushed together to form an implant assembly, the formation of the implant assembly will itself assist in vertebral distraction, as follows. Each of implants 20 may also have tops 23 and bottoms 25 which are angled to elongated member 30, as shown. An first advantage of having slanting tops 23 and bottoms 25 is that as inserts 20A to 20C are sequentially advanced over elongated member 30 toward knot 31, successive inserts 20A to 20C will each be slightly taller than the previously inserted implant such that successive inserts tend to pry apart (i.e.: distract) the adjacent vertebrae. A second advantage of having tops 23 and bottoms 25 slant both as shown in FIG. 6 and as in FIG. 5 is that together such slanting will give the implants a tapered shape which assists in providing a preferred lordotic angle between the adjacent vertebrae. It is to be understood that to achieve a proper lordotic angle, each of implants 20A, 20B, 20C, etc. may be shaped slightly differently depending upon the final location (around the endplate perimeter) at which the respective implant is to be positioned. (FIG. 6 is shown in an exploded view with the angles of tops 23 and bottoms 25 exaggerated for clarity of illustration purposes).

Figure 7:
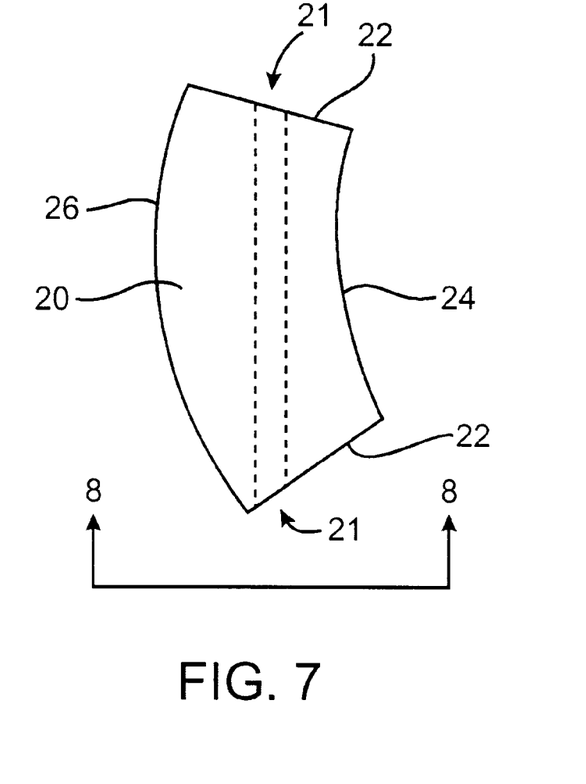
FIG. 7 is a top plan view of a single intervertebral implant.
Figure 8:
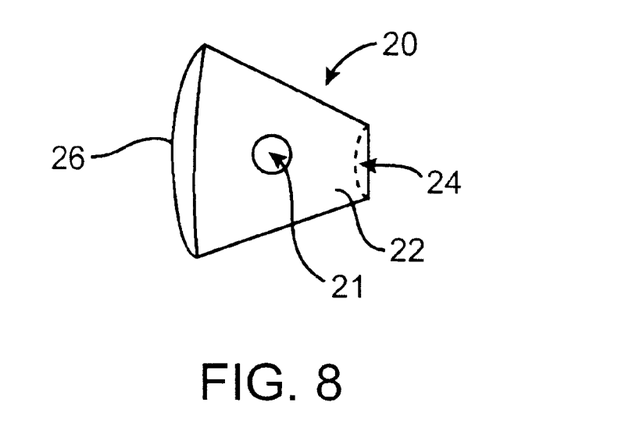
FIG. 8 is a side elevation view taken along line 8—8 in FIG. 7.

FIGS. 7 and 8 show further details of the preferred geometry of a single intervertebral implant 20.

Figure 9:
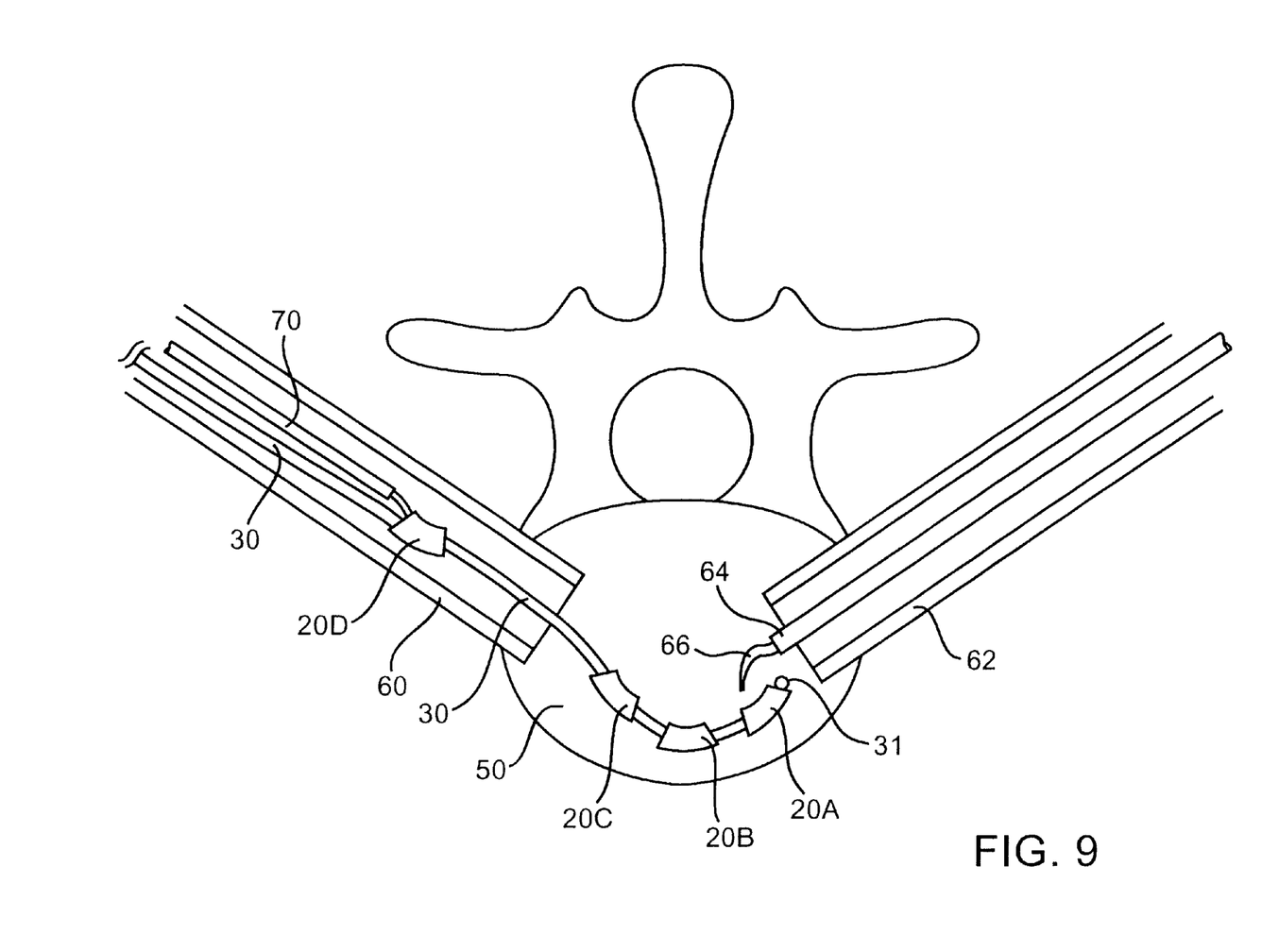
FIG. 9 is an illustration of a preferred method of placement of the intervertebral implants.

FIG. 9 shows an optional preferred method of inserting implants 20A, 20B and 20C in which elongated member 30 is inserted into the patient's intervertebral space, and implants 20A, 20B and 20C are sequentially inserted over elongated member 30. A positioning rod 64 (having a hook 66 at its distal end) is advanced through a second operating cannula 62 and is used to manually adjust the positioning of each of implants 20A, 20B and 20C. As can also be seen, a positioning tool 70 can be inserted through operating cannula 60, to both advance implant 20D distally forward (such that it together forms an implant support assembly 10 with implants 20A, 20B and 20C), and to push against implant 20D when elongated member 30 is withdrawn (i.e.: pulled taught) in cannula 60.

Figure 10:
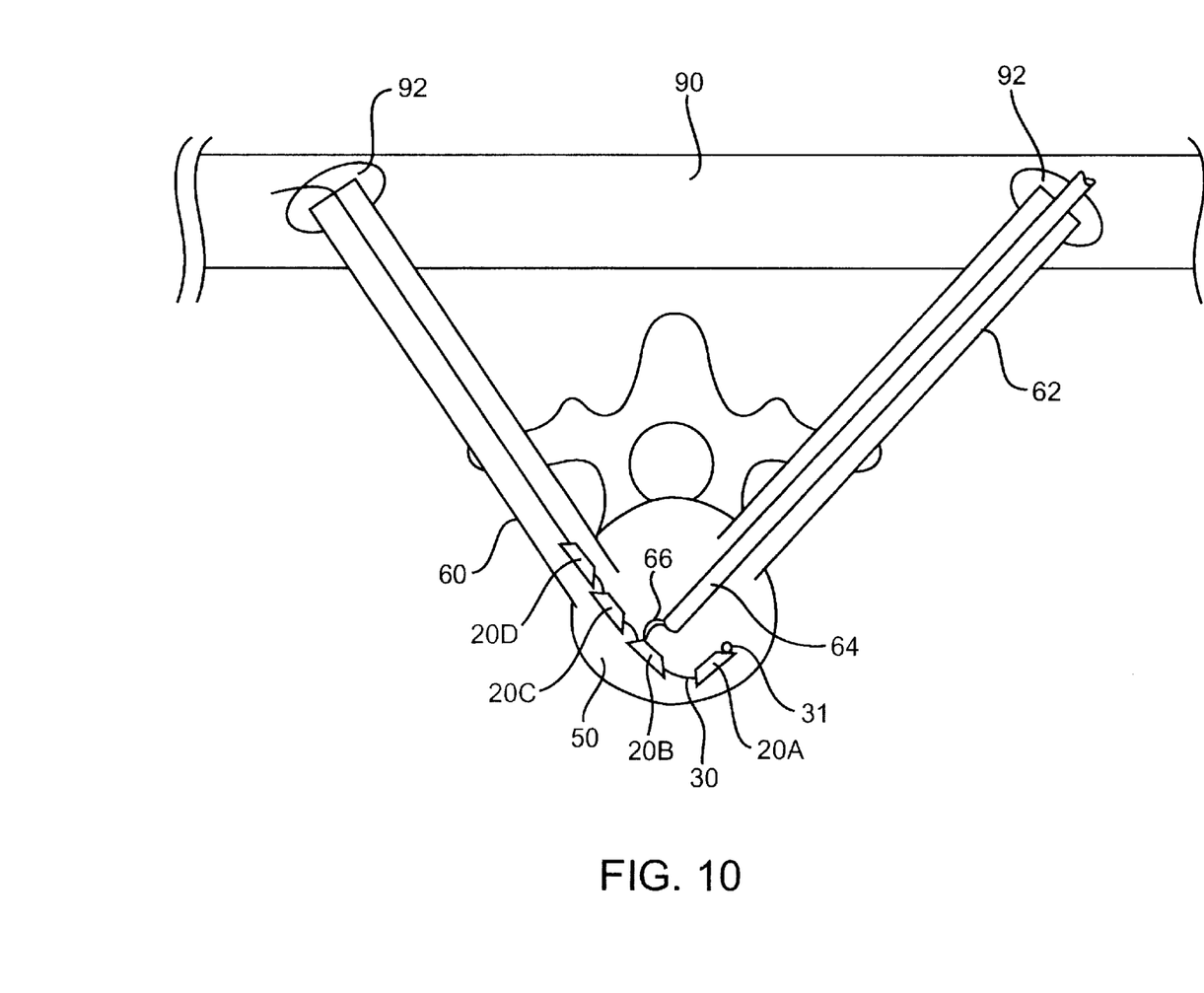
FIG. 10 is an illustration of a preferred method of placement of the intervertebral implants using a surgical guideframe with operating cannulae supported by the surgical guideframe.

FIG. 10 illustrated a preferred method of placement of the intervertebral implants using a surgical guideframe 90 with operating cannulae supported by cannula guides 92 of surgical guideframe 90, and is ideally suited to be performed with the surgical guideframe set forth in Applicant's co-pending U.S. patent application Ser. No. 09/326,739, filed Jun. 4, 1999, and incorporated herein by reference in its entirety for all purposes.

Figures 11A, 11B:
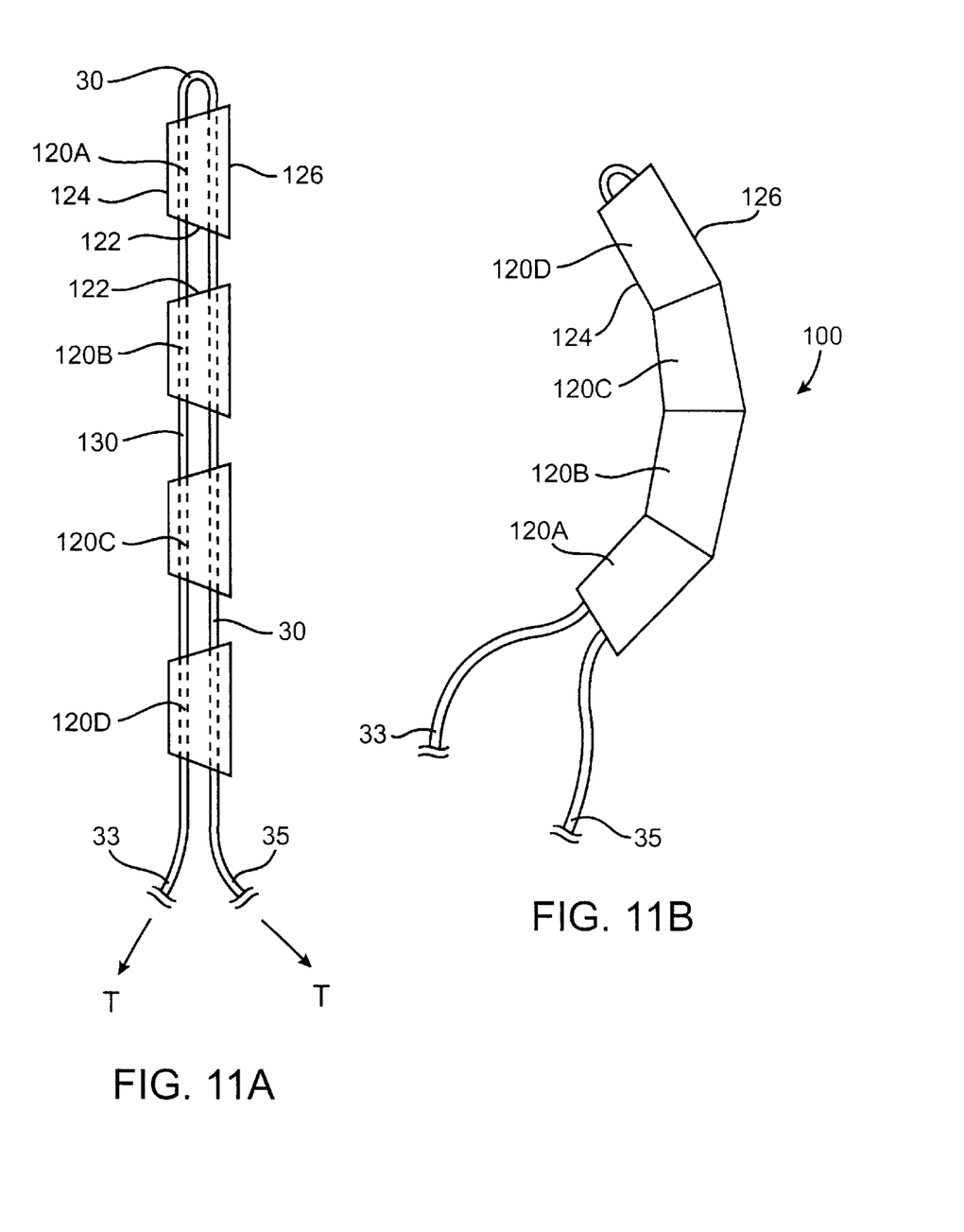
FIG. 11A shows a plurality of intervertebral implants spaced apart on an elongated member, the elongated member being received twice through each implant.
FIG. 11B shows a plurality of intervertebral implants pushed together on an elongated member, the elongated member being received twice through each implant.

FIGS. 11A and 11B show a plurality of implants 120A, 120B, 120C and 120D, each having two parallel holes passing therethrough such that elongated member 30 may be threaded back and forth therethrough, (as partially shown in dotted lines in FIG. 11A). As elongated member 30 is pulled taught, (i.e.: with ends 33 and 35 being pulled taught in directions T), a curved shaped intervertebral assembly 100 will be formed.

As also show in FIGS. 11A and 11B, implants 120 may have straight sides 124 and 126, (as opposed to curved sides 24 and 26 of implants 20. As can be seen, ends 122 of implants 120 are preferably angled to a central longitudinal axis extending through the implant parallel to the holed through which elongated member 30 is received.

An advantage of the aspect of the invention shown in FIGS. 11A and 11B is that (having parallel holes passing through each of the implants 120) stability will be enhanced. Moreover, elongated member 30 may be cut (after assembly 100 is formed) such that ends 33 and 35 can simply be tied, or otherwise fused, together.

In any of the above aspects of the invention where elongated member 30 passes through one or two hole(s) in each of the implants, the elongated member may be cut and tied (or fused into a knot) at the proximal end of the assembly such that it securely holds the plurality of implants together in an assembly. As such, a portion of elongated member 30 preferably remains within the patient's intervertebral space, tying (or otherwise securing) the separate implants together and-to-end forming the preferred interveretebral implant assembly.

What is claimed is:

1. An intervertebral implant system, comprising:
   a plurality of implants, each implant having at least one hole passing therethrough; and
   an elongated member dimensioned to pass through the holes in each of the plurality of implants, wherein the plurality of implants are slidingly movable over the elongated member, and wherein the plurality of implants can be positioned to abut against one another.

2. The intervertebral implant system of claim 1, wherein, the elongated member is selected from the group consisting of a cord, string, tether or suture.

3. The intervertebral implant system of claim 1, wherein, the elongated member comprises braided suture material.

4. The intervertebral implant system of claim 1, wherein, the elongated member comprises a flexible wire.

5. The intervertebral implant system of claim 4, wherein, the wire is made of a shape-memory metal.

6. The intervertebral implant system of claim 1, wherein, the at least one hole comprises two holes passing through each of the intervertebral implants.

7. The intervertebral implant system of claim 6, wherein, the two holes pass through each of the intervertebral implants in parallel to one another.

8. The intervertebral implant system of claim 7, wherein, a single elongated member is threaded through both of the holes.

9. The intervertebral implant system of claim 1, wherein, at least some of the plurality of intervertebral implants have ends which are angled to a central longitudinal axis extending through the implant.

10. The intervertebral implant system of claim 9, wherein, the plurality of intervertebral implants form a curved assembly when the angled ends of the implants are abutted together end-to-end.

11. The intervertebral implant system of claim 1, wherein, at least some of the plurality of intervertebral implants have top and bottom surfaces which are angled to one another such that the plurality of intervertebral implants form an assembly which tapers in a lordotic angle when the implants are abutted together end-to-end.

12. The intervertebral implant system of claim 1, wherein, each implant has two curved sides, and wherein one of the curved sides is concave and the other curved side is convex.

13. The intervertebral implant system of claim 1, further comprising:
   a positioning rod for adjusting the position of each of the intervertebral implants.

14. The intervertebral implant system of claim 13, further comprising:
   first and second operating cannula, wherein the elongated member and the plurality of implants are dimensioned to be received through the first operating cannula, and the positioning rod is dimensioned to be received through the second operating cannula.

15. The intervertebral implant system of claim 14, further comprising:
   a surgical guideframe adapted to support the first and second operating cannula.

16. A method of positioning a plurality of intervertebral implants in a patient's intervertebral space, comprising:
   introducing an elongated member into the patient's intervertebral space; and
   sequentially advancing a plurality of intervertebral implants over the elongated member and into the patient's intervertebral space, the plurality of intervertebral implants each having at least one hole passing therethrough, with the elongated member received through the holes passing through each of the plurality of implants.

17. The method of claim 16, wherein sequentially advancing the plurality of intervertebral implants comprises:
   advancing the plurality of intervertebral implants over the elongated member such that they abut one against another.

18. The method of claim 16, wherein the elongated member passes through two holes in each implant.

19. The method of claim 17, wherein advancing the plurality of intervertebral implants over the elongated member such that they abut one against another, comprises:
   distally pushing on the last of the sequence of intervertebral implants, thereby causing the implants to abut together, forming a curved implant assembly.

20. The method of claim 19, wherein distally pushing on the last of the sequence of intervertebral implants comprises pushing with a positioning rod.

21. The method of claim 17, wherein advancing the plurality of intervertebral implants over the elongated member such that they abut one against another, comprises:
drawing back on the elongated member, thereby causing the plurality of intervertebral implants to abut together, forming a curved implant assembly.

22. The method of claim 19 or 21, wherein, at least some of the plurality of intervertebral implants have ends which are angled to a central longitudinal axis extending through the implant.

23. The method of claim 21, wherein the curved implant assembly is positioned around a portion of the perimeter of the patient's intervertebral space.

24. The method of claim 16, further comprising:
positioning at least some of the plurality of intervertebral implants with a positioning rod.

25. The method of claim 16, further comprising:
cutting the elongated member such that a portion of the elongated member passing through the plurality of intervertebral implants remains disposed therein after the remainder of the elongated member has been removed from the intervertebral space.

26. The method of claim 25, further comprising:
forming a knot in an end of the portion of the elongated member passing through the plurality of intervertebral implants such that the plurality of intervertebral implants are held together.

27. The method of claim 25, further comprising:
connecting together separate ends of the portion of the elongated member passing through the plurality of intervertebral implants such that the plurality of intervertebral implants are held together.

28. The method of claim 16, wherein, the elongated member and the plurality of intervertebral implants are advanced through a first operating cannula into the intervertebral space, the first operating cannula being supported in a surgical guideframe.

29. The method of claim 28, wherein, a positioning rod is advanced through a second operating cannula into the intervertebral space, the second operating cannula being supported in a surgical guideframe.

30. An intervertebral implant system, comprising:
a plurality of implants, each implant having at least one hole passing therethrough; and
an elongated member dimensioned to pass through the holes in each of the plurality of implants, wherein, the at least one hole comprises two parallel holes passing through each of the intervertebral implants, and wherein the elongated member is threaded through both of the holes.

31. An intervertebral implant system, comprising:
a plurality of implants, each implant having at least one hole passing therethrough; and
an elongated member dimensioned to pass through the holes in each of the plurality of implants, and wherein at least some of the plurality of intervertebral implants have ends which are angled to a central longitudinal axis extending through the implant, and wherein the plurality of intervertebral implants form a curved assembly when the angled ends of the implants are abutted together end-to-end.

32. An intervertebral implant system, comprising:
a plurality of implants, each implant having at least one hole passing therethrough; and
an elongated member dimensioned to pass through the holes in each of the plurality of implants, wherein each implant has two curved sides, and wherein one of the curved sides is concave and the other curved side is convex.

33. An intervertebral implant system, comprising:
a plurality of implants, each implant having at least one hole passing therethrough; and
an elongated member dimensioned to pass through the holes in each of the plurality of implants;
a positioning rod for adjusting the position of each of the intervertebral implants; and
first and second operating cannula, wherein the elongated member and the plurality of implants are dimensioned to be received through the first operating cannula, and the positioning rod is dimensioned to be received through the second operating cannula.

34. An intervertebral implant system, comprising:
a plurality of implants, each implant having at least one hole passing therethrough; and
an elongated member dimensioned to pass through the holes in each of the plurality of implants;
a positioning rod for adjusting the position of each of the intervertebral implants;
first and second operating cannula, wherein the elongated member and the plurality of implants are dimensioned to be received through the first operating cannula, and the positioning rod is dimensioned to be received through the second operating cannula; and
a surgical guideframe adapted to support the first and second operating cannula.

* * * * *

UNITED STATES PATENT AND TRADEMARK OFFICE
Certificate

Patent No. 6,387,130 B1　　　　　　　　　　　　　　　　　　　　　　　　Patented: May 14, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Corbett W. Stone, San Diego, CA (US); James F. Marino, La Jolla, CA (US); and Bryan Cornwall, San Diego, CA (US).

Signed and Sealed this Eleventh Day of October 2011.

THOMAS SWEET
*Supervisory Patent Examiner*
Art Unit 3738
Technology Center 3700